United States Patent
Takeuchi et al.

(10) Patent No.: US 11,913,895 B2
(45) Date of Patent: Feb. 27, 2024

(54) METHOD FOR DETECTING OCCURRENCE OF CRACKS AND THE LIKE, DEVICE FOR DETECTING OCCURRENCE OF CRACKS AND THE LIKE, AND PROGRAM FOR DETECTING OCCURRENCE OF CRACKS AND THE LIKE

(71) Applicant: Nippon Telegraph and Telephone Corporation, Tokyo (JP)

(72) Inventors: Yosuke Takeuchi, Musashino (JP); Takuya Kamisho, Musashino (JP); Masamitsu Watanabe, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 595 days.

(21) Appl. No.: 15/734,654

(22) PCT Filed: May 28, 2019

(86) PCT No.: PCT/JP2019/021116
§ 371 (c)(1),
(2) Date: Dec. 3, 2020

(87) PCT Pub. No.: WO2019/235303
PCT Pub. Date: Dec. 12, 2019

(65) Prior Publication Data
US 2021/0231596 A1    Jul. 29, 2021

(30) Foreign Application Priority Data
Jun. 5, 2018 (JP) .................................. 2018-107429

(51) Int. Cl.
*G01N 27/20* (2006.01)
*G01N 3/08* (2006.01)

(52) U.S. Cl.
CPC ............... *G01N 27/20* (2013.01); *G01N 3/08* (2013.01)

(58) Field of Classification Search
CPC .......... G01N 17/02; G01N 27/20; G01N 3/08; G01N 33/2045; G01N 2203/0062; G01N 2203/0064; G01N 2203/024
(Continued)

(56) References Cited

U.S. PATENT DOCUMENTS

2016/0363525 A1* 12/2016 Friedersdorf ............ G01N 3/06

FOREIGN PATENT DOCUMENTS

JP    H01-269041 A    10/1989
JP    H01269041    * 10/1989    ............. G01N 27/00
(Continued)

OTHER PUBLICATIONS

Tetsushi Chida et al., *Comparison of Constant Load, SSRT and CSRT Methods for Hydrogen Embrittlement Evaluation Using Round Bar Specimens of High Strength Steels*, Iron and Steel Tetsu-to-Hagane, vol. 100, No. 10, 2014, pp. 1298-1305.
(Continued)

*Primary Examiner* — Jermele M Hollington
*Assistant Examiner* — Courtney G Mcdonnough
(74) *Attorney, Agent, or Firm* — Workman Nydegger (57) ABSTRACT

To easily detect a crack having occurred in a steel material. A current measurement device measures a value of a current flowing through a target steel material that is immersed in an electrolyte aqueous solution and applied with tensile stress while subjected to hydrogen charging, and a device for detecting the occurrence of a crack or the like uses the measured current value to determine the occurrence of a crack in the target steel material when the amount of change in the current flowing through the target steel material, the change rate of the amount of change in the current, or the
(Continued)

change rate of the change rate of the amount of change in the current exceeds a threshold value. The device for detecting the occurrence of a crack or the like determines the occurrence of a crack in the steel material when the change rate of the change rate of the amount of change in the current is less than a negative value of an absolute value of the threshold value, and determines the occurrence of fracture in the steel material when the change rate exceeds the absolute value of the threshold value.

4 Claims, 4 Drawing Sheets

(58) Field of Classification Search
USPC .......................................................... 324/718
See application file for complete search history.

(56) References Cited

FOREIGN PATENT DOCUMENTS

| JP | 2015-169466 A | 9/2015 | |
| JP | 2015169466 A * | 9/2015 | ............. G01N 17/02 |
| JP | 2017-187441 A | 10/2017 | |

OTHER PUBLICATIONS

Shingo Yamasaki et al., *Delayed Fracture Mechanism in High Strength Steels by Acoustic Emission Source Wave Analysis*, Iron and Steel Tetsu-to-Hagane, vol. 83, No. 7, 1997, pp. 460-465.

Ryo Abe et al., *Hydrogen Release Behavior During Tensile Deformation of SUS316L Steel that has Undergone Hydrogen Embrittlement*, Spring Lecture Meeting of the Japan Institute of Metals, 2007, pp. 1.

* cited by examiner

METHOD FOR DETECTING OCCURRENCE OF CRACKS AND THE LIKE, DEVICE FOR DETECTING OCCURRENCE OF CRACKS AND THE LIKE, AND PROGRAM FOR DETECTING OCCURRENCE OF CRACKS AND THE LIKE

TECHNICAL FIELD

The present invention relates to a technique for detecting the occurrence of a crack or fracture of a steel material caused by hydrogen embrittlement.

BACKGROUND ART

At present, the research and development of steel materials with good hydrogen embrittlement resistance have been actively advanced with the aim of energy savings of moving bodies and the like by strength increases and weight savings of steel materials, and the aim of low costs of materials and members in hydrogen gas facilities such as hydrogen stations.

However, a steel material has a problem of hydrogen embrittlement in which the steel material becomes brittle when hydrogen enters metal which is the steel material and stress is applied to the metal, and it is known that the phenomenon of hydrogen embrittlement occurs more prominently in a steel material with higher strength. Therefore, it has been considered important to evaluate the hydrogen embrittlement resistance of the steel material.

In the case of evaluating the hydrogen embrittlement resistance of the steel material, the steel material is subjected to hydrogen charging, stress is applied to the steel material, and an acceleration test for controlling the stress and the entry of hydrogen is performed to produce a fractured state in a short time. The acceleration test method has also been examined with various improvements, and in many evaluation methods, the hydrogen embrittlement resistance of the steel material is evaluated based on the occurrence or non-occurrence of fracture within an arbitrarily set predetermined time or the length of time until the occurrence of fracture (Non-Patent Literature 1).

On the other hand, a steel material that is actually used for equipment as a material or a member is broken over a longer period of time under actual conditions. Thus, for improving the hydrogen embrittlement resistance of the steel material, it is important to understand the breaking process due to hydrogen embrittlement.

However, in the evaluation method for the hydrogen embrittlement resistance performed by the conventional hydrogen embrittlement resistance test, it has been difficult to stop the test before breaking because the breaking proceeds rapidly, and it has been difficult to observe the breaking process inside the steel material.

Hence a technique for observing the fracture surface of the steel material after breaking has been used as the main evaluation method of the breaking process, but the fracture surface of the steel material with hydrogen embrittlement is often in a mixed state with a cleavage fracture surface or a grain-boundary fracture surface called a pseudo cleavage fracture surface, and it is known to be difficult to make an interpretation such as whether or not the fracture surface is caused by hydrogen embrittlement.

In order to observe the growth of a crack inside the steel material, the stress having been applied to the steel material need be removed at the time of occurrence of the crack, but the occurrence of the crack need be detected before the removal. As such a method for detecting the occurrence of a crack, that is, a method for detecting a sign of breaking in the steel material, an acoustic emission method has been developed to measure an acoustic wave corresponding to elastic energy emitted from the inside upon breaking of the steel material (Non-Patent Literature 2).

CITATION LIST

Non-Patent Literature

Non-Patent Literature 1: "Comparison of Constant Load, SSRT and CSRT Methods for Hydrogen Embrittlement Evaluation Using Round Bar Specimens of High Strength Steels," written by Senda and eight others, Iron and Steel, Vol. 100, No. 10, 2014, p. 1298-p. 1305

Non-Patent Literature 2: "Delayed Fracture Mechanism in High Strength Steels by Acoustic Emission Source Wave Analysis," written by Yamazaki and one other, Iron and Steel, The Iron and Steel Institute of Japan, Vol. 83, No. 7, 1997, p. 460-p. 465

SUMMARY OF THE INVENTION

Technical Problem

However, in a case where the acoustic emission method is used to detect the occurrence of a crack inside the steel material, a special jig is required for detecting an acoustic wave from the inside of the steel material, and noise need be removed from the detected acoustic wave, thereby causing a problem such as lack of convenience.

The present invention has been made in view of the above circumstances, and it is an object of the present invention to easily detect a crack having occurred in a steel material.

Means for Solving the Problem

In a method for detecting the occurrence of a crack or the like according to the present invention, a current measurement device performs a measurement step of measuring a value of a current flowing through a steel material that is applied with tensile stress while subjected to hydrogen charging; and a device for detecting the occurrence of a crack or the like performs a determination step of using the measured current value to determine the occurrence of a crack in the steel material when an amount of change in the current flowing through the steel material, a change rate of the amount of change in the current, or a change rate of the change rate of the amount of change in the current exceeds a threshold value.

In the method for detecting the occurrence of a crack or the like, in the determination step, the occurrence of a crack in the steel material is determined when the change rate of the change rate of the amount of change in the current is less than a negative value of an absolute value of the threshold value, and the occurrence of fracture in the steel material is determined when the change rate exceeds the absolute value of the threshold value.

A method for detecting the occurrence of a crack or the like according to the present invention, performed by using a device for detecting the occurrence of a crack or the like, performs: an input step of receiving input of a value of a current flowing through a steel material that is applied with tensile stress while subjected to hydrogen charging, and storing the value into a storage unit; and a determination step of reading out the current value from the storage unit and determining the occurrence of a crack in the steel material when an amount of change in the current flowing through the steel material, a change rate of the amount of change in the current, or a change rate of the change rate of the amount of change in the current exceeds a threshold value.

A device for detecting the occurrence of a crack or the like according to the present invention includes: an input unit that receives input of a value of a current flowing through a steel material that is applied with tensile stress while subjected to hydrogen charging, and stores the value into a storage unit; and a determination unit that reads out the current value from the storage unit, and determines the occurrence of a crack in the steel material when an amount of change in the current flowing through the steel material, a change rate of the amount of change in the current, or a change rate of the change rate of the amount of change in the current exceeds a threshold value.

A program for detecting the occurrence of a crack or the like according to the present invention causes a computer to function as the above device for detecting the occurrence of a crack or the like.

Effects of the Invention

According to the present invention, it is possible to easily detect a crack having occurred in a steel material.

BRIEF DESCRIPTION OF DRAWINGS

FIG. 5 is a diagram showing a processing flow of a method for detecting the occurrence of a crack or the like.

DESCRIPTION OF EMBODIMENTS

Conventionally, in the evaluation technique for hydrogen embrittlement resistance in the hydrogen embrittlement resistance test where the steel material is electrochemically charged with hydrogen to evaluate its resistance, the evaluation has been performed based on the time until the steel material fractures as described in the background art.

The present invention enables detection of a crack having occurred in the steel material by adding, to the conventional technique as thus described, a mechanism for monitoring a current flowing through the steel material and a mechanism for comparing the value of the current flowing through the steel material with a threshold value to determine the presence or absence of a crack. By monitoring a change in the value of the current flowing through the steel material, it is possible to easily detect the occurrence of a crack. By removing the stress having been applied to the steel material while detecting the occurrence of a crack, it is possible to stop the test before the breaking of the steel material and evaluate the breaking process due to hydrogen embrittlement. Hereinafter, an embodiment of the present invention will be described with reference to the drawings.

Figure 1:
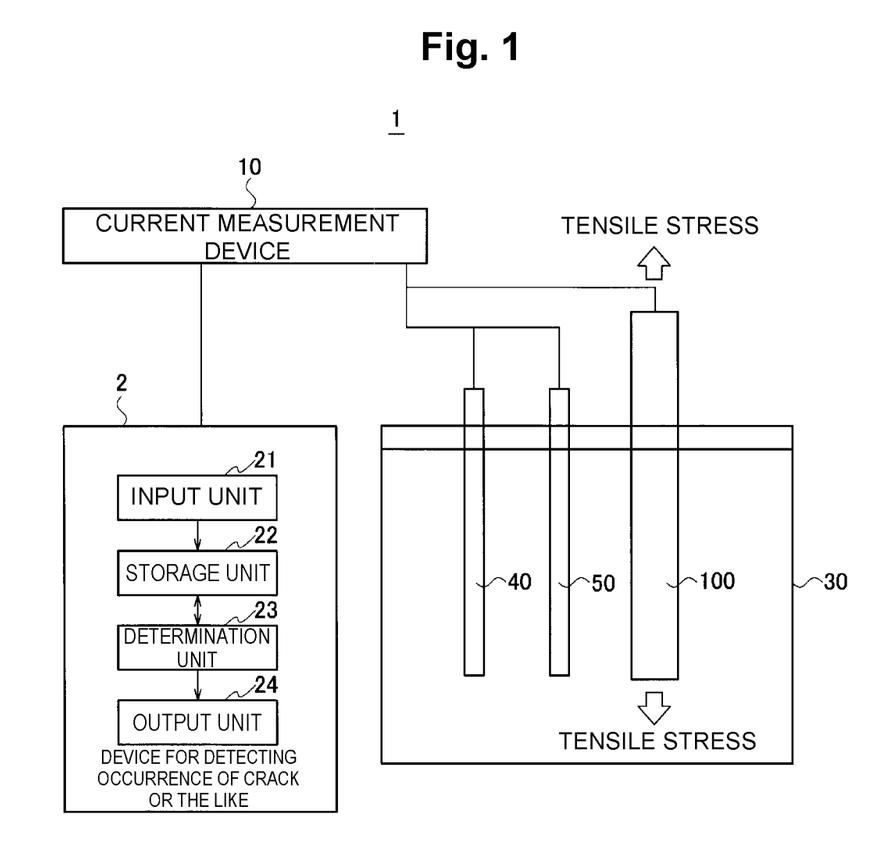
FIG. 1 shows an overall configuration of a system.

FIG. 1 is a diagram schematically showing an overall configuration of a system according to the present embodiment. A system 1 is a test system for evaluating hydrogen embrittlement resistance of a steel material and includes: a current measurement device 10 that measures a value of a current flowing through a target steel material 100 to be evaluated; and a device 20 for detecting the occurrence of a crack or the like that detects the current value measured by the current measurement device 10 to detect a crack or fracture having occurred in the target steel material 100.

The current measurement device 10 is a measurement instrument required for electrochemical measurement, and for example, a potentiostat is used. The device 20 for detecting the occurrence of a crack or the like is configured using a computer provided with a central processing unit (CPU), a memory, a hard disk, a monitor, a communication interface, a keyboard, a mouse, and the like, for example.

As shown in FIG. 1, the device 20 for detecting the occurrence of a crack or the like includes an input unit 21, a storage unit 22, a determination unit 23, and an output unit 24. The input unit 21 receives input of the value of the current flowing through the target steel material 100 measured by the current measurement device 10. The storage unit 22 stores the input current value. The determination unit 23 reads out the current value from the storage unit 22, and determines that a crack or fracture has occurred in the target steel material 100 when the amount of change in the current, the change rate of the amount of change in the current, or the change rate of the change rate of the amount of change in the current exceeds a threshold value. The output unit 24 outputs data, such as the determination result, the current value, and the threshold value, to the monitor as a graph or the like.

The input unit 21 of the device 20 for detecting the occurrence of a crack or the like may be a reception unit that receives data of the value of the current flowing through the target steel material 100 when the device 20 for detecting the occurrence of a crack or the like is communicably connected to the current measurement device 10 and the current measurement device 10 is capable of transmitting the data of the current value. The current measurement device 10 and the device 20 for detecting the occurrence of a crack or the like may be combined to physically constitute one device.

Although not shown in FIG. 1, the system 1 also includes a stress application device that applies tensile stress to each end of the target steel material 100. The stress application device may be communicably connected to each of the current measurement device 10 and the device 20 for detecting the occurrence of a crack or the like.

Next, a description will be given of a method for a constant load test on the target steel material 100 and a measurement method for the current flowing through the target steel material 100, which are performed using the current measurement device 10.

In the present embodiment, the constant load test is performed to apply tensile stress to the target steel material 100 while electrochemically charging the target steel material 100 with hydrogen. The application method for tensile stress may be a method of applying a constant load or a method of increasing a load with the passage of time.

In a case where a constant load is applied, the greater the tensile stress to apply, the shorter the test time can be made. However, the tensile stress to apply is desirably in an elastic stress region and is thus set to, for example, stress of 0.7 times the tensile strength of the target steel material 100 (0.7 $\sigma_b$). For example, a round bar smooth material having a length of 50 cm and a diameter of 7 mm is used as a test piece of the target steel material 100.

As a method for performing the hydrogen charging, for example, as shown in FIG. 1, a cathode charging method is used in which the target steel material 100 is immersed into an electrolyte aqueous solution 30, and a negative potential is applied. As the electrolyte aqueous solution 30, for example, a 1-mol/L sodium hydrogen carbonate aqueous solution is used.

Hydrogen is generated on the surface of the steel material by controlling the potential with the target steel material 100 as a working electrode. As a counter electrode 40 of the target steel material 100, for example, an insoluble electrode such as platinum is used, and as a reference electrode 50, for example, a silver/silver chloride electrode is used. For the reference electrode 50, a commercially available one need only be selected arbitrarily. An applied voltage to be applied to the target steel material 100 need only impart a potential difference sufficient to generate hydrogen on the surface of the steel material and be set to, for example, −1 Vvs. SSE.

Figure 2:
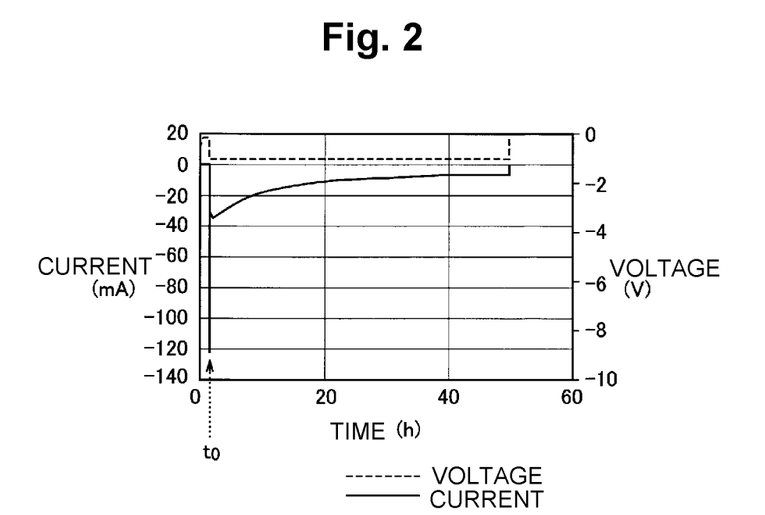
FIG. 2 is a diagram showing an example of a change in a current value in a case where a steel material is not broken.
Figure 3:
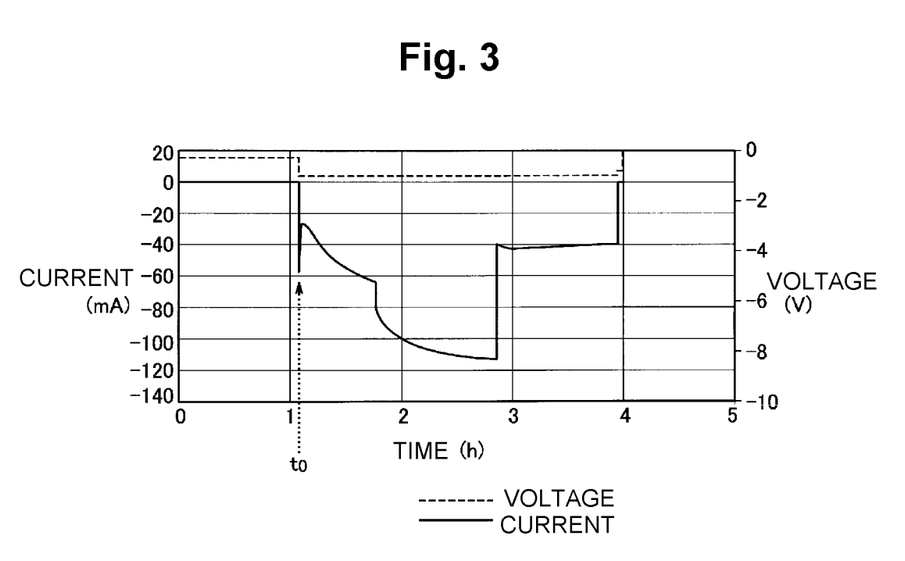
FIG. 3 is a diagram showing an example of the change in the current value in a case where the steel material is broken.

FIGS. 2 and 3 show changes in the current when a constant load is applied to the target steel material 100. FIG. 2 shows an example of the change in the current value in a case where the steel material is not broken, and FIG. 3 shows an example of the change in the current value in a case where the steel material is broken.

In the case where the steel material is not broken, as shown in FIG. 2, after the application of the voltage at time to, the value of the current flowing through the target steel material 100 gradually changes due to exposure of a metal base or a change in liquid properties accompanying the reduction of an oxide film.

On the other hand, in the case where the steel material is broken, as shown in FIG. 3, the value of the current flowing through the target steel material 100 after the application of the voltage at time to greatly changes due to the occurrence of a crack or fracture. When a crack occurs, the current value increases as an area of contact with the solution increases. At the time of the fracture, only a part of the steel material connected to the current measurement device 10 (the upper portion of the target steel material 100 shown in FIG. 1) becomes a working electrode, and the area in contact with the solution decreases, so that the current value decreases.

The measurement results of the current shown in FIGS. 2 and 3 are the current change characteristics of the target steel material 100, and when the amount of change in the current or the change rate of the amount of change in the current exceeds an arbitrary threshold value X, it is possible to determine the occurrence of a crack or fracture by using the current change characteristic shown in FIG. 3. In the present embodiment, the current measurement device 10 periodically measures the value of the current flowing through the target steel material 100 that is applied with the tensile stress while subjected to hydrogen charging. When the measured amount of change in the current, change rate of the amount of change in the current, or change rate of the change rate of the amount of change in the current exceeds the arbitrary threshold value X, the device 20 for detecting the occurrence of a crack or the like determines the occurrence of a crack or fracture in the target steel material 100.

For example, when the amount of change in the current is A, the change rate of the amount A of change is B, the change rate of the change rate B is C, the current is I, and the time is t, $A=dI=I_n-I_{n-1}$ (n is a natural number), $B=dI/dt$, and $C=d^2I/dt^2$. Any of A, B, and C need only be used to determine the occurrence of a crack or fracture.

The threshold value X need only be the maximum value of the amount of change in a predetermined unit time, obtained from measurement data measured in the case where the steel material does not fracture. The threshold values corresponding to the change rates B and C are, for example, the change rate of the "maximum value of the amount of change" and the change rate of the change rate of the "maximum value of the amount of change." In a case where the measurement data of the non-fracturing steel material is not used, the threshold value X need only be determined using a value in a region of a gentle current change as shown in FIG. 2 in which no crack occurs. The occurrence of a more minimal crack can be detected as the threshold value X is made smaller.

Next, a method for detecting the occurrence of a crack or the like will be described. Hereinafter, the description will be given using the change rate C.

Figure 4:
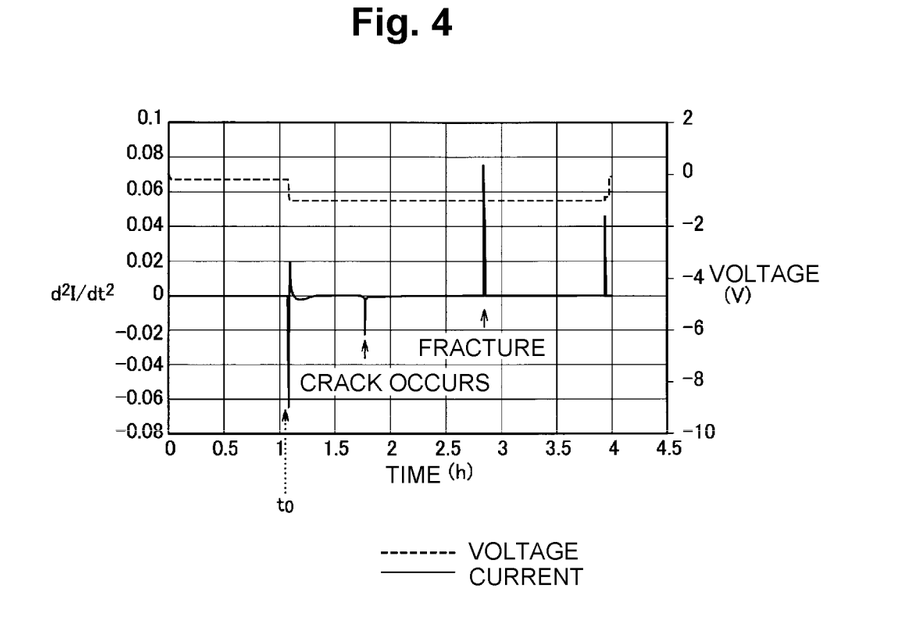
FIG. 4 is a diagram showing an example of a change in the second derivative of the current value in the case where the steel material is broken.

FIG. 4 shows an example of a change in the change rate $C(=d^2I/dt^2)$ obtained from the current I in FIG. 3. Assuming that the value of the change rate C (e.g., average value) for about 30 minutes after the application of the voltage at time to is the threshold value X and $|X|=0.0001$ mA/s², for example, when the change rate C is less than −|X|, it is determined that a crack has occurred in the steel material, and when the change rate C exceeds |X|, it is determined that fracture has occurred in the steel material. The current value greatly varies immediately after the application of the voltage due to generation of a non-faradaic current, reduction of the oxide film, or the like, and it is thus desirable to set an arbitrary standby time (e.g., 10 minutes) and perform the determination of the threshold value X and the processing for detecting the occurrence of a crack.

Figure 5:
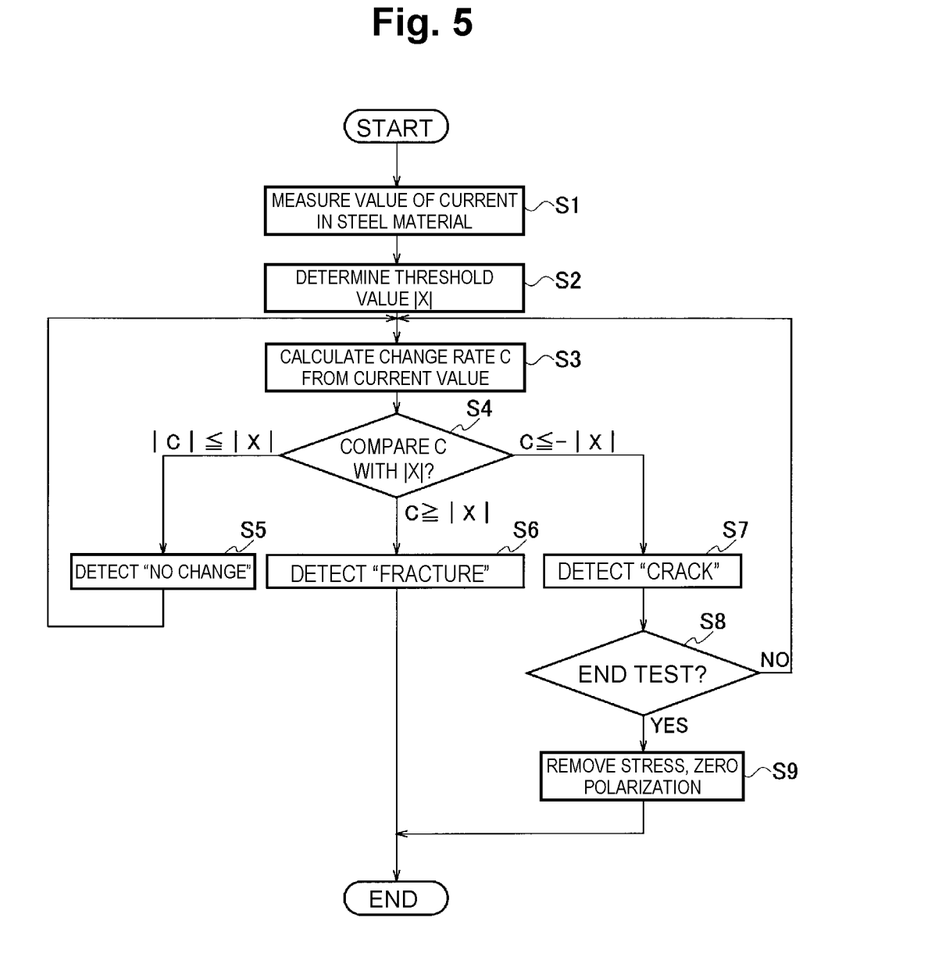

Next, with reference to FIGS. 1 and 5, the processing operation of the method for detecting the occurrence of a crack or the like will be described.

First, the current measurement device 10 periodically measures a value $I_n$ of a current flowing through the target steel material 100 that is applied with the tensile stress while subjected to hydrogen charging. The input unit 21 of the device 20 for detecting the occurrence of a crack or the like then receives input of the measured current value $I_n$ and stores the input current value $I_n$ into the storage unit 22 (step S1).

Next, the determination unit 23 of the device 20 for detecting the occurrence of a crack or the like determines the threshold value X to be used with respect to the change rate C based on the current change characteristic of the target steel material 100 (step S2). At this time, the device 20 for detecting the occurrence of a crack or the like may calculate and determine the threshold value X by itself based on the current change characteristic of the target steel material 100 or may determine a set value set by a tester as it is as the threshold value X.

Next, the determination unit 23 of the device 20 for detecting the occurrence of a crack or the like reads out the value $I_n$ of the current having flowed from the storage unit 22 to the target steel material 100 and calculates the change rate $C(=d^2I/dt^2)$ by using the read-out current value $I_n$ (step S3).

Then, the determination unit 23 of the device 20 for detecting the occurrence of a crack or the like compares the change rate C with |X| which is the absolute value of the threshold value X, and proceeds to step S5 when $|C|\leq|X|$, proceeds to step S6 when $|C|\geq|X|$, and proceeds to step S7 when $|C|\leq-|X|$ (step S4). Note that "<" or ">" may be used in place of "≤" or "≥", and the tester can make a selection as appropriate.

In the case of ICI IN, the determination unit 23 of the device 20 for detecting the occurrence of a crack or the like determines that no fracture or crack has occurred in the target steel material 100, detects a state of "no change in the target steel material 100", returns to step S3, and executes steps S3 and S4 by using a current value $I_{n+1}$ measured at the next timing (step S5).

In the case of |C|≤|X|, the determination unit 23 of the device 20 for detecting the occurrence of a crack or the like determines that the target steel material 100 has fractured, detects a state of "fracture has occurred in the target steel material 100", and ends the processing (step S6).

In the case of C≤−|X|, the determination unit 23 of the device 20 for detecting the occurrence of a crack or the like determines that a crack has occurred in the target steel material 100, and detects a state of "the target steel material 100 having a crack" (step S7).

After step S7, the determination unit 23 of the device 20 for detecting the occurrence of a crack or the like causes the tester to determine whether or not to end the test (step S8). When the tester selects to continue the test, the processing returns to step S3, and steps S3 and S4 are executed using a current value $I_{n+1}$ measured at the next timing.

On the other hand, when the tester selects to end the test, the tester removes the tensile stress having been applied to the target steel material 100 by using the stress application device, and sets the applied voltage to the target steel material 100 to 0 by using the current measurement device 10 (step S9). Thereafter, the processing is ended.

In step S9, instead of the tester manually removing the tensile stress and setting the applied voltage to 0, the operation may be automated so that the output unit 24 of the device 20 for detecting the occurrence of a crack or the like transmits a stress change request for changing the tensile stress value to 0 to the stress application device and transmits a voltage change request for changing the applied voltage to 0 to the current measurement device 10 based on a designation to end the test by the tester.

According to the present embodiment, the current measurement device 10 measures the value of the current flowing through the target steel material 100 that is immersed in the electrolyte aqueous solution 30 and applied with tensile stress while subjected to hydrogen charging. Then, the device 20 for detecting the occurrence of a crack or the like uses the measured current value to determine that a crack or fracture has occurred in the target steel material 100 when the amount of change in the current flowing through the target steel material 100, the change rate of the amount of change in the current, or the change rate of the change rate of the amount of change in the current exceeds the threshold value. That is, whether or not a crack or fracture has occurred in the target steel material 100 is determined based on the amount of change in the current flowing through the target steel material 100, the change rate of the amount of change in the current, or the change rate of the change rate of the amount of change in the current. This eliminates the need for the special jig for detecting an acoustic wave used in the acoustic emission method, so that it is possible to easily detect a crack or fracture having occurred in the steel material.

Finally, the current measurement device 10 and the device 20 for detecting the occurrence of a crack or the like can also be achieved by a computer and a program, and the program can be both recorded on a recording medium and provided over a network.

REFERENCE SIGNS LIST

1 System
10 Current measurement device
20 Device for detecting occurrence of crack or the like
21 Input unit
22 Storage unit
23 Determination unit
24 Output unit
30 Electrolyte aqueous solution
40 Counter electrode
50 Reference electrode
100 Target steel material

The invention claimed is:

1. A method for detecting occurrence of a crack or the like, comprising:
a measurement step of, by a current measurement device, measuring a value of a current flowing through a steel material that is applied with tensile stress, the current generated by the steel material being subjected to a hydrogen charging process of immersing the steel material in an aqueous solution and applying a negative potential to the steel material; and
a determination step of, by a device for detecting occurrence of a crack or the like, using the measured current value to determine occurrence of a crack in the steel material when an amount of change in the current flowing through the steel material, a change rate of the amount of change in the current, or a change rate of the change rate of the amount of change in the current exceeds a threshold value,
wherein in the determination step, occurrence of a crack in the steel material is determined when the change rate of the amount of change in the current is less than a negative value of an absolute value of the threshold value, and occurrence of fracture in the steel material is determined when the change rate exceeds the absolute value of the threshold value.

2. A method for detecting occurrence of a crack or the like, performed by using a device for detecting occurrence of a crack or the like, comprising:
an input step of receiving input of a value of a current flowing through a steel material that is applied with tensile stress, the current generated by the steel material being subjected to a hydrogen charging process of immersing the steel material in an aqueous solution and applying a negative potential to the steel material, and storing the value into a storage unit; and
a determination step of reading out the current value from the storage unit and determining occurrence of a crack in the steel material when an amount of change in the current flowing through the steel material, a change rate of the amount of change in the current, or a change rate of the change rate of the amount of change in the current exceeds a threshold value,
wherein in the determination step, occurrence of a crack in the steel material is determined when the change rate of the amount of change in the current is less than a negative value of an absolute value of the threshold value, and occurrence of fracture in the steel material is determined when the change rate exceeds the absolute value of the threshold value.

3. A device for detecting occurrence of a crack or the like, comprising:
an input unit that receives input of a value of a current flowing through a steel material that is applied with tensile stress, the current generated by the steel material being while subjected to a hydrogen charging process of immersing the steel material in an aqueous solution and applying a negative potential to the steel material, and stores the value into a storage unit; and
a determination unit that reads out the current value from the storage unit, and determines occurrence of a crack in the steel material when an amount of change in the current flowing through the steel material, a change rate of the amount of change in the current, or a change rate of the change rate of the amount of change in the current exceeds a threshold value, wherein occurrence of a crack in the steel material is determined when the change rate of the amount of change in the current is less than a negative value of an absolute value of the threshold value, and occurrence of fracture in the steel material is determined when the change rate exceeds the absolute value of the threshold value.

4. A program for detecting occurrence of a crack or the like, causing a computer to function as the device for detecting occurrence of a crack or the like according to claim 3.

* * * * *